(12) United States Patent
Locke et al.

(10) Patent No.: US 12,186,159 B2
(45) Date of Patent: Jan. 7, 2025

(54) HYBRID ADHESIVE TISSUE COVER WITH APPLICATION STRETCH

(71) Applicant: Solventum Intellectual Properties Company, Maplewood, MN (US)

(72) Inventors: Christopher Brian Locke, Bournemouth (GB); Timothy Mark Robinson, Shillingstone (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 429 days.

(21) Appl. No.: 17/602,476

(22) PCT Filed: Mar. 20, 2020

(86) PCT No.: PCT/US2020/023888
§ 371 (c)(1),
(2) Date: Oct. 8, 2021

(87) PCT Pub. No.: WO2020/219196
PCT Pub. Date: Oct. 29, 2020

(65) Prior Publication Data
US 2022/0202622 A1 Jun. 30, 2022

Related U.S. Application Data

(60) Provisional application No. 62/838,162, filed on Apr. 24, 2019.

(51) Int. Cl.
*A61F 13/00* (2024.01)
*A61F 13/0203* (2024.01)
*A61F 13/05* (2024.01)

(52) U.S. Cl.
CPC ...... *A61F 13/022* (2013.01); *A61F 13/00085* (2013.01); *A61F 13/05* (2024.01)

(58) Field of Classification Search
None
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Kim M Lewis (57) ABSTRACT

A cover for protecting a tissue site may comprise a shell layer, an adhesive disposed on the shell layer, and a contact layer disposed adjacent to the adhesive. The contact layer may have a first pattern of apertures and bridges, and the shell layer may have a second pattern of apertures overlaying the bridges. In some examples, the adhesive may have a bond strength that is greater than the tensile modulus of the shell layer. The contact layer may have an open area of about 40 percent to about 50 percent of the total area of the contact layer. A release liner may be disposed adjacent to the contact layer. Perforations through the shell layer and the contact layer can define a sacrificial segment configured to be separated from the shell layer and the contact layer. A handling bar may be coupled to the sacrificial segment.

20 Claims, 7 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,158,555 A * | 10/1992 | Porzilli ............... A61F 13/0203 604/304 |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2014/0163491 A1 | 6/2014 | Schuessler et al. |
| 2015/0080788 A1 | 3/2015 | Blott et al. |
| 2016/0144085 A1 | 5/2016 | Melin et al. |
| 2018/0110657 A1 | 4/2018 | Locke et al. |
| 2018/0353336 A1 | 12/2018 | Locke et al. |
| 2018/0353337 A1 | 12/2018 | Locke |
| 2020/0146899 A1* | 5/2020 | Pratt .................. A61F 13/0243 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |

(56) References Cited

FOREIGN PATENT DOCUMENTS

| WO | 94/20041 A1 | 9/1994 |
|---|---|---|
| WO | 96/05873 A1 | 2/1996 |
| WO | 97/18007 A1 | 5/1997 |
| WO | 99/13793 A1 | 3/1999 |
| WO | 2010134873 A1 | 11/2010 |
| WO | 2013090810 A1 | 6/2013 |
| WO | 2014097069 A1 | 6/2014 |
| WO | 2018/125739 A1 | 7/2018 |
| WO | 2020097497 A1 | 5/2020 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
"D.E. Tribble, An Improved Sump Drain-Irrigation Device of Simple Construction," Archives of Surgery 105 (1972) pp. 511-513.
M.J. Morykwas, L.C. Argenta, E.I. Shelton-Brown, and W. McGuirt, "Vacuum-Assisted Closure: a New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: a Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for Corresponding Application No. PCT/US2020/023888 mailed Jun. 9, 2020.
Chinese First Office Action Corresponding to Application No. 2020800308834, mailed Jun. 15, 2022.
Japanese Notice of Rejection for corresponding application 2021-560860, dated Jun. 11, 2024.
Japanese Notice of Rejection for corresponding application 2021-560860, dated Jan. 23, 2024.

\* cited by examiner

HYBRID ADHESIVE TISSUE COVER WITH APPLICATION STRETCH

RELATED APPLICATIONS

The present application claims priority to U.S. Provisional Patent Application No. 62/838,162, entitled "Hybrid Adhesive Tissue Cover with Application Stretch," filed Apr. 24, 2019, which is incorporated herein by reference for all purposes.

TECHNICAL FIELD

The invention set forth in the appended claims relates generally to tissue treatment systems and more particularly, but without limitation, to systems, apparatuses, and methods for covering tissues sites.

BACKGROUND

Dressings are generally considered standard care for many types of tissue treatment, particularly for treating wounds. Regardless of the etiology of a wound, whether trauma, surgery, or another cause, proper care of the wound is important to the outcome. Dressings can provide many functions that can be beneficial for healing wounds, including controlling the wound environment and protecting a wound from bacteria and further physical trauma.

While the benefits of dressings are widely known, improvements to dressing technology can benefit healthcare providers and patients.

BRIEF SUMMARY

New and useful systems, apparatuses, and methods for treating tissue are set forth in the appended claims. Illustrative embodiments are also provided to enable a person skilled in the art to make and use the claimed subject matter.

For example, in some embodiments, dressings and covers for treating tissue may be configured to stretch and deform during application without the inherent spring force of the dressing or cover overcoming the adhesive system. In some examples, a suitable cover may comprise a silicone layer having perforations and a polymer film having a pattern of fenestrations that align between the perforations in the silicone layer. The fenestrations may be between about 2 millimeters and about 5 millimeters in length, and may have a spacing of between 2 millimeters and 5 millimeters between fenestrations. The fenestrations may be arranged to maintain the structural integrity of the film when fenestrated. The laminated film and silicone structure can deform, with the silicone layer stretching and thinning as it elongates. The polymer film may also allow stretch with a low force, and the fenestrations can move an open as the structure is moved and elongated.

In some embodiments the polymer film may be very thin and not fenestrated. The thin film retains a very low level of elasticity, and can be bonded to a perforated and fenestrated silicone layer. Thus, elasticity in the silicone layer may be reduced or removed, leaving the polymer film as the only source of elasticity in the structure.

In some embodiments, the polymer film may have an elastic limit that is below the bond strength of the weakest adhesive in the system. The film may be selected to have a low elastic limit so that higher forces result in the material exceeding its elastic limit and permanently deforming while retaining its integrity.

Additionally or alternatively, the film may be lightly embossed, which can provide a store of film that can become available in a low-elastic form if stretched.

More generally, a cover for protecting a tissue site may comprise a shell layer, an adhesive disposed on the shell layer, and a contact layer disposed adjacent to the adhesive. The contact layer may have a first pattern of apertures and bridges, and the shell layer may have a second pattern of apertures overlaying the bridges. In some examples, the adhesive may have a bond strength that is greater than the tensile modulus of the shell layer.

In some embodiments, the contact layer may have an open area of about 40 percent to about 50 percent of the total area of the contact layer. Perforations through the shell layer and the contact layer can define a sacrificial segment configured to be separated from the shell layer and the contact layer. A handling bar may be coupled to the sacrificial segment. A release liner may be disposed adjacent to the contact layer.

In some examples, the open area may be formed by a plurality of holes through the contact layer, and at least some of the plurality of holes may be arranged in a row having a midline substantially aligned with the perforations. The perforations may have a cut length of about 2 millimeters and a tie length of about 1 millimeter in some examples. Additionally or alternatively, some embodiments of the handling bar may be at least partially disposed between the shell layer and the contact layer. For example, the handling bar may be at least partially disposed between the shell layer and the contact layer exterior to the perforations.

The shell layer may comprise a polymer film, such as a drape. In more particular examples, the shell layer may comprise a polyurethane film. The contact layer may comprise a silicone gel in some examples.

In other examples, an apparatus for protecting a tissue site may comprise a contact layer, a drape, and a release liner. The contact layer generally may have a first edge and a second edge parallel to the first edge. The contact layer may additionally have a plurality of apertures, which can be arranged in a first row having a first midline parallel to the first edge and a second row having a second midline parallel to the second edge. The drape may have an adhesive on one side, wherein at least some of the adhesive is disposed adjacent to the plurality of apertures. The drape may be coextensive with the contact layer in some examples. The drape and the contact layer may have a first line of perforations, and the first line of perforations can be aligned with the first midline. The drape and the contact layer may additionally have a second line of perforations, and the second line of perforations may be aligned with the second midline. A first handling bar may be partially disposed between the contact layer and the drape exterior to the first line of perforations, and a second handling bar partially disposed between the contact layer and the shell layer exterior to the second line of perforations. In some examples, the apparatus may additionally include a release liner adjacent to the contact layer.

A method of manufacturing a cover for a tissue site is also describe herein. In some examples, the method may comprise perforating a contact layer, disposing a handling bar on the contact layer, disposing a barrier layer having an adhesive on the contact layer over the handling bar, perforating the barrier layer and the contact layer along an interior edge of the handling bar, and disposing a release liner on the contact layer.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
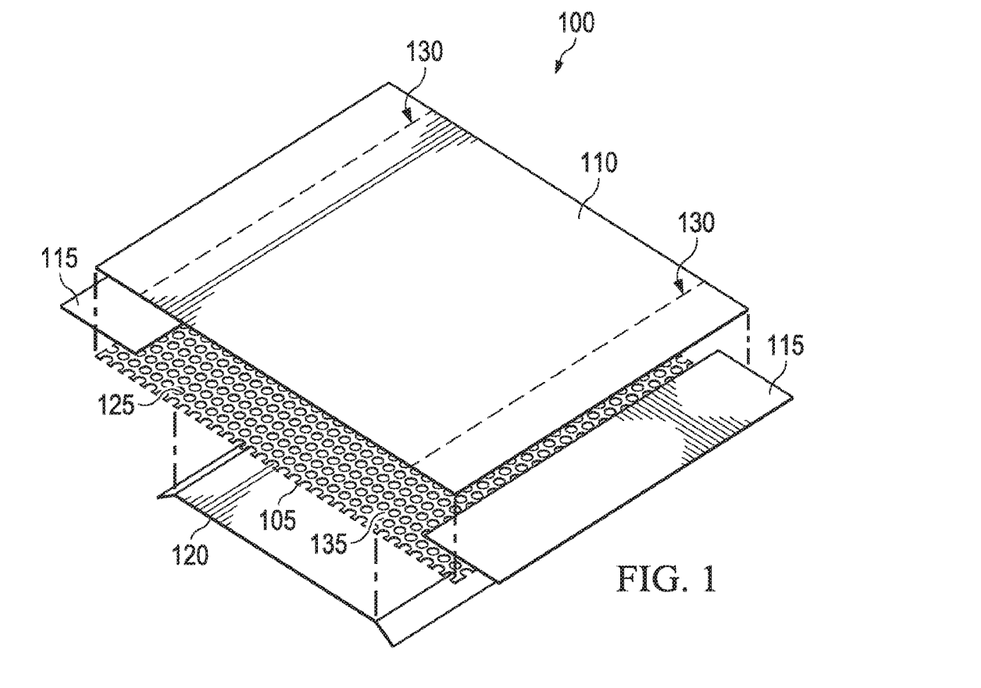
FIG. 1 is an assembly view of a cover that can be applied a tissue site.

FIG. 1 is an assembly view of an example of a cover 100, which can be applied to a tissue site. The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, a tissue site may be used to grow additional tissue that can be harvested and transplanted.

The cover 100 of FIG. 1 generally includes a contact layer 105 and a shell layer 110. As illustrated in the example of FIG. 1, the cover 100 may additionally include one or more handling bars 115 and a release liner 120. As illustrated in the example of FIG. 1, the contact layer 105 and the shell layer 110 may have apertures. For example, the contact layer 105 of FIG. 1 has a plurality of apertures 125 and the shell layer 110 has a plurality of apertures 130. Areas between apertures in the contact layer 105, the shell layer 110, or both may be characterized as bridges or ties. For example, the contact layer 105 may have bridges 135 between the apertures 125.

In some embodiments, the contact layer 105 may comprise or consist essentially of a soft, pliable material suitable. The contact layer 105 may also have an adherent or tacky surface. For example, the contact layer 105 may comprise or consist essentially of a tacky gel having a peel adhesion of about 0.2 to 0.3 N/cm (180 degree peel on stainless steel). The contact layer 105 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the contact layer 105 may have a thickness between about 200 microns (μm) and about 1000 microns (μm). In some embodiments, the contact layer 105 may have a hardness between about 5 Shore OO and about 80 Shore OO. Further, the contact layer 105 may be comprised of hydrophobic or hydrophilic materials.

In some embodiments, the contact layer 105 may be a coated material. For example, the contact layer may be formed by coating a porous material, such as, for example, a woven, a nonwoven, or an extruded mesh with a hydrophobic material. The hydrophobic material for the coating may be a soft silicone, for example.

In some embodiments, the shell layer 110 may provide a bacterial barrier and protection from physical trauma. The shell layer 110 may also be constructed from a material that can reduce evaporative losses and provide a fluid seal between two components or two environments, such as between a therapeutic environment and a local external environment. The shell layer 110 may comprise or consist of, for example, an elastomeric film or membrane that can provide a seal adequate to maintain a negative pressure at a tissue site for a given negative-pressure source. The shell layer 110 may have a high moisture-vapor transmission rate (MVTR) in some applications. For example, the MVTR may be at least 250 grams per square meter per twenty-four hours (g/m$^2$/24 hours) in some embodiments, measured using an upright cup technique according to ASTM E96/E96M Upright Cup Method at 38° C. and 10% relative humidity (RH). In some embodiments, an MVTR up to 5,000 g/m$^2$/24 hours may provide effective breathability and mechanical properties.

In some example embodiments, the shell layer 110 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The shell layer 110 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis, Minnesota; polyurethane (PU) drape, commercially available from Avery Dennison Corporation, Pasadena, California; polyether block polyamide copolymer (PEBAX), for example, from Arkema S. A., Colombes, France; and Inspire 2301 and Inpsire 2327 polyurethane films, commercially available from Expopack Advanced Coatings, Wrexham, United Kingdom. In some embodiments, the shell layer 110 may comprise INSPIRE 2301 having an MVTR (upright cup technique) of 2600 $g/m^2/24$ hours and a thickness of about 30 microns.

An attachment device may be disposed on a side of the shell layer 110. The attachment device may take many forms. For example, an attachment device may be a medically-acceptable, pressure-sensitive adhesive disposed on a side of the shell layer 110 facing the contact layer 105. At least some of the adhesive may be disposed adjacent to the apertures 125. In some embodiments, for example, some or all of one side of the shell layer 110 may be coated with an adhesive, such as an acrylic adhesive, which may have a coating weight of about 25-65 grams per square meter (g.s.m.). Other example embodiments of an attachment device may include a double-sided tape, paste, hydrocolloid, hydrogel, silicone gel, or organogel.

In some configurations, additional layers (not shown) may be disposed between the shell layer 110 and the contact layer. For example, a scrim layer may be used with an adhesive to facilitate manufacture, or an absorbent may be disposed between portions of the contact layer 105 and the shell layer 110.

The release liner 120 may be configured to protect the contact layer 105 and any adhesive prior to use. The release liner may be embossed in some examples. The release liner 120 may comprise two or more release panels in some embodiments. For example, the release liner 120 may comprise one or more panels that can be positioned along opposing edges of the contact layer 105. A first release panel may overlap or otherwise extend over a portion of a second release panel in some embodiments. In other embodiments, the release liner 120 may additionally have a third release panel, which can overlap or otherwise extend over a portion of at least one of the other release panels. In some embodiments, the release liner 120 may have the same size as the contact layer 105. The release liner 120 may also have one or more release tabs, which may be integral to or otherwise coupled to one or more release panels in some embodiments.

The release liner 120 (or one or more release panels) may comprise or consist essentially of a casting paper or a polymer film, for example. In some embodiments, the release liner 120 may comprise or consist of a polyethylene film. Further, in some embodiments, the release liner 120 may be a polyester material such as polyethylene terephthalate (PET), or similar polar semi-crystalline polymer. The use of a polar semi-crystalline polymer for the release liner 120 may substantially preclude wrinkling or other deformation of the cover 100. For example, a polar semi-crystalline polymer may be highly orientated and resistant to softening, swelling, or other deformation that may occur when brought into contact with components of the cover 100, or when subjected to temperature or environmental variations, or sterilization. Further, a release agent may be disposed on a side of the release liner 120 that is configured to contact the contact layer 105. For example, the release agent may be a silicone coating and may have a release factor suitable to facilitate removal of the release liner 120 by hand and without damaging or deforming the cover 100. In some embodiments, the release agent may be a fluorocarbon or a fluorosilicone, for example. In other embodiments, the release liner 120 may be uncoated or otherwise used without a release agent.

Figure 2:
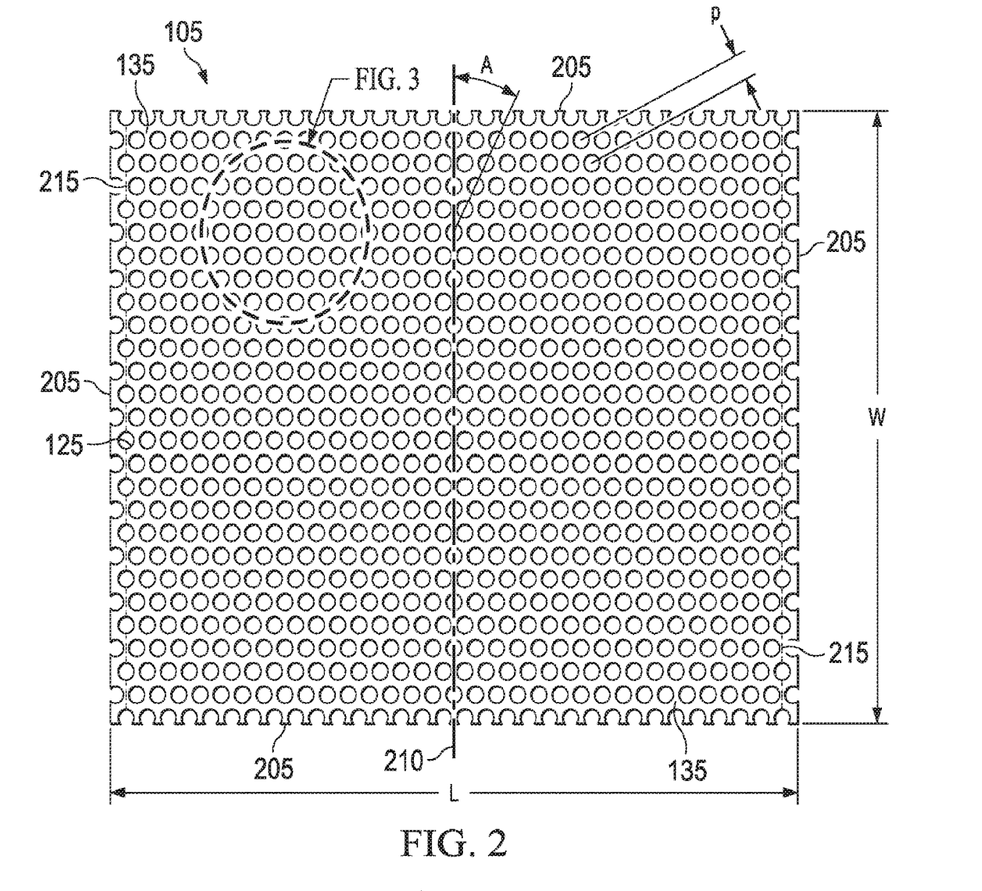
FIG. 2 is a top view of an example of a contact layer that may be associated with some embodiments of the cover of FIG. 1.
Figure 3:
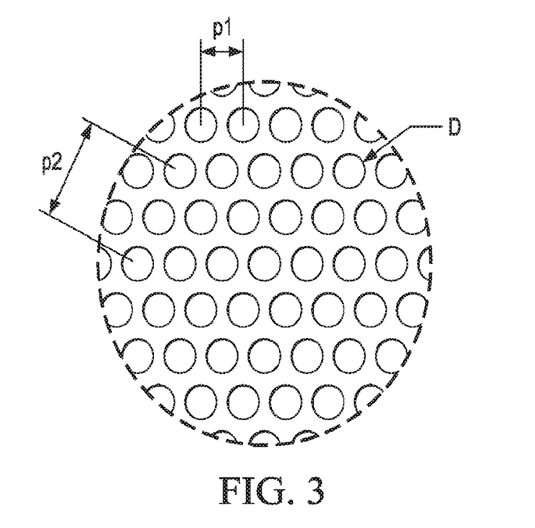
FIG. 3 is a detail view of the contact layer of FIG. 2.

FIG. 2 is a top view of an example of the contact layer 105, illustrating additional details that may be associated with some embodiments. FIG. 3 is a detail view of the contact layer 105 in the example of FIG. 2, illustrating additional details that may be associated with some embodiments. In the example of FIG. 2, the contact layer 105 is rectangular, having edges 205, a width W, and a length L. The apertures 125 may be characterized by various properties, such as hole shape, hole size, hole pattern, and pattern orientation.

The apertures 125 may have many shapes, including circles, squares, stars, ovals, polygons, slits, complex curves, rectilinear shapes, triangles, or some combination of such shapes.

The size of the apertures 125 may be specified by a single dimension in some examples, such as a width of a circle or a square. In some examples, the size may be specified by a length (the longer of two dimensions) and width (the shorter of two dimensions). In some embodiments, each of the apertures 125 may have a width of about 1 millimeter to about 50 millimeters. A width of about 6 millimeters to about 8 millimeters may be suitable for some embodiments. Each of the apertures 125 may have uniform or similar sizes. For example, in some embodiments, each of the apertures 125 may have substantially the same width. In other embodiments, geometric properties of the apertures 125 may vary. For example, the width of the apertures 125 may vary depending on the position of the apertures 125 in the contact layer 105. In some embodiments, the width of the apertures 125 may be larger in a peripheral area than an interior area of the contact layer 105. At least some of the apertures 125 may be positioned on one or more of the edges 205 of the contact layer 105, and may have an interior cut open or exposed at the edges 205.

The apertures 125 may be arranged in a pattern. For example, the apertures 125 may have a uniform distribution pattern, such as an arrangement of rows, or may be randomly distributed in the contact layer 105. Rows may be staggered in some examples. The stagger may be characterized by an orientation relative to an edge or other reference line associated with the contact layer 105. For example, the stagger may be characterized by an angle A between a midline 210 of the contact layer 105 and a line through the midpoints of the apertures 125 in adjacent rows parallel to the edges 205. The angle A may vary. For example, a stagger of about 45 degrees or about 60 degrees may be suitable for some embodiments. A pattern may also be characterized by a pitch P, which indicates the spacing between the centers of apertures. Some patterns may be characterized by a single pitch value; others may be characterized by at least two pitch values. For example, if the spacing between centers of the apertures 125 is the same in all orientations, the pitch P may be characterized by a single value indicating the diagonal spacing between centers of the apertures 125 in adjacent rows.

The contact layer 105 may also be characterized by an open area, which can be formed by the apertures 125. The open area may be expressed as a percentage of an area defined by edges of the contact layer 105, such as the area defined by the edges 205 in the example of FIG. 2. An open area of about 40 percent to about 50 percent of the area of the contact layer 105 may be suitable for some examples.

As illustrated in the example of FIG. 2, some embodiments of the contact layer 105 may additionally have a plurality of apertures 215. The apertures 215 may be characterized by various properties, such as hole shape, hole size, hole pattern, and pattern orientation. In FIG. 2, the apertures 215 may be characterized as slots, for example. The size of slots generally may be characterized by a length, which may be specified as a "cut length." A cut length of about 2 millimeters may be suitable for some examples. The apertures 215 of FIG. 2 are arranged in a linear pattern in which all of the apertures 215 are aligned parallel to one of the edges 205. The linear pattern may be characterized by the spacing between the apertures 215, which may be referred to as a bridge or tie. A tie length of about 1 millimeter may be suitable for some examples. As illustrated in the example of FIG. 2, the midline of the apertures 215 may be aligned with a midline of a row of the apertures 125. More specifically, in some examples, the midline of the apertures 215 may be aligned with a peripheral row of the apertures 125 that is parallel to the shorter of the edges 205. Peripheral rows are generally characterized as rows of the apertures 125 that are closest to the edges 205, exclusive of rows in which some or all of the apertures 125 are exposed or partially open on the edges 205. In some embodiments, the midline of the apertures 215 may be aligned with interior rows, which are interior to the peripheral rows.

As illustrated in the example of FIG. 3, the apertures 125 may be circular holes having a width D. A width D of about 7 millimeters may be suitable for some examples. FIG. 3 further illustrates an example in which pitch is specified by two values, p1 and p2, indicating the center spacing of the apertures 125 in aligned rows orthogonal to the edges 205. If p1 and p2 are not equal, then p1 is indicative of the shorter pitch. In the example of FIG. 3, p1 may be about 9.8 millimeters and p2 may be about 17 millimeters. The example values of D, p1, and p2 forms an open area of about 46 percent of the area defined by the edges 205 of FIG. 2.

Figure 4:
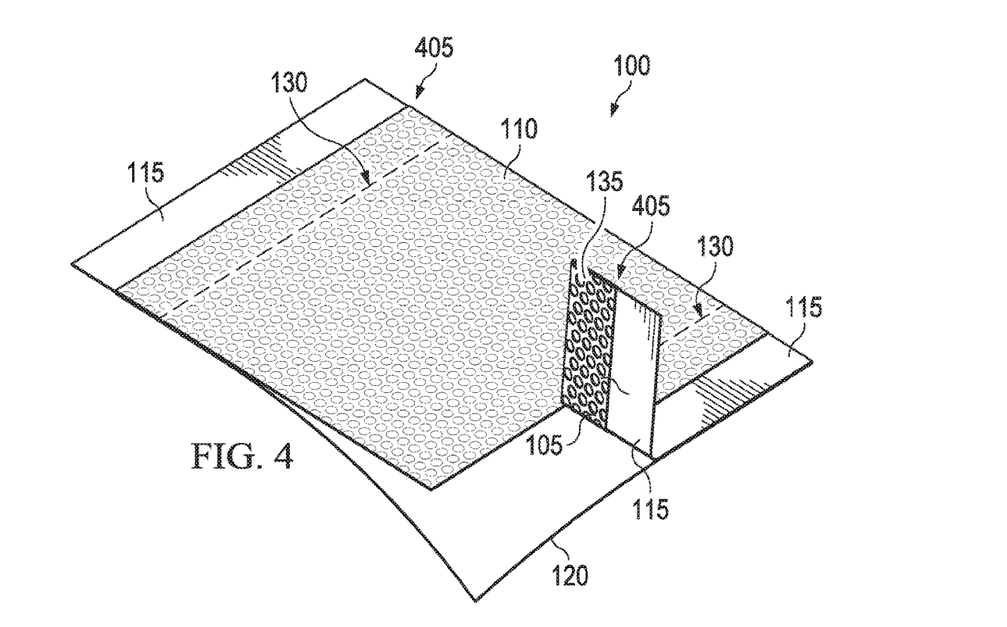
FIG. 4 is a perspective view of an example of the cover of FIG. 1, illustrating additional details that may be associated with some embodiments.

FIG. 4 is a perspective view of an example of the cover 100, illustrating additional details that may be associated with some embodiments. In FIG. 4, the apertures 130 in the shell layer 110 and the apertures 215 (not visible in FIG. 4) in the contact layer 105 are aligned and define one or more sacrificial segments 405. Each of the handling bars 115 may be coupled to one of the sacrificial segments 405. For example, each of the handling bars 115 may be at least partially laminated or otherwise disposed between the contact layer 105 and the shell layer 110. In some examples, an interior edge of the handling bars 115 may be exterior to the apertures 130 and the apertures 215, and the handling bars 115 may extend past the edges of the contact layer 105 and the shell layer 110.

In some embodiments, the shell layer 110 and the contact layer 105 may be coextensive. The release liner 120 may be coextensive with the contact layer 105, and may extend past the contact layer 105 to coincide with exterior edges of the handling bars 115.

Figure 5:
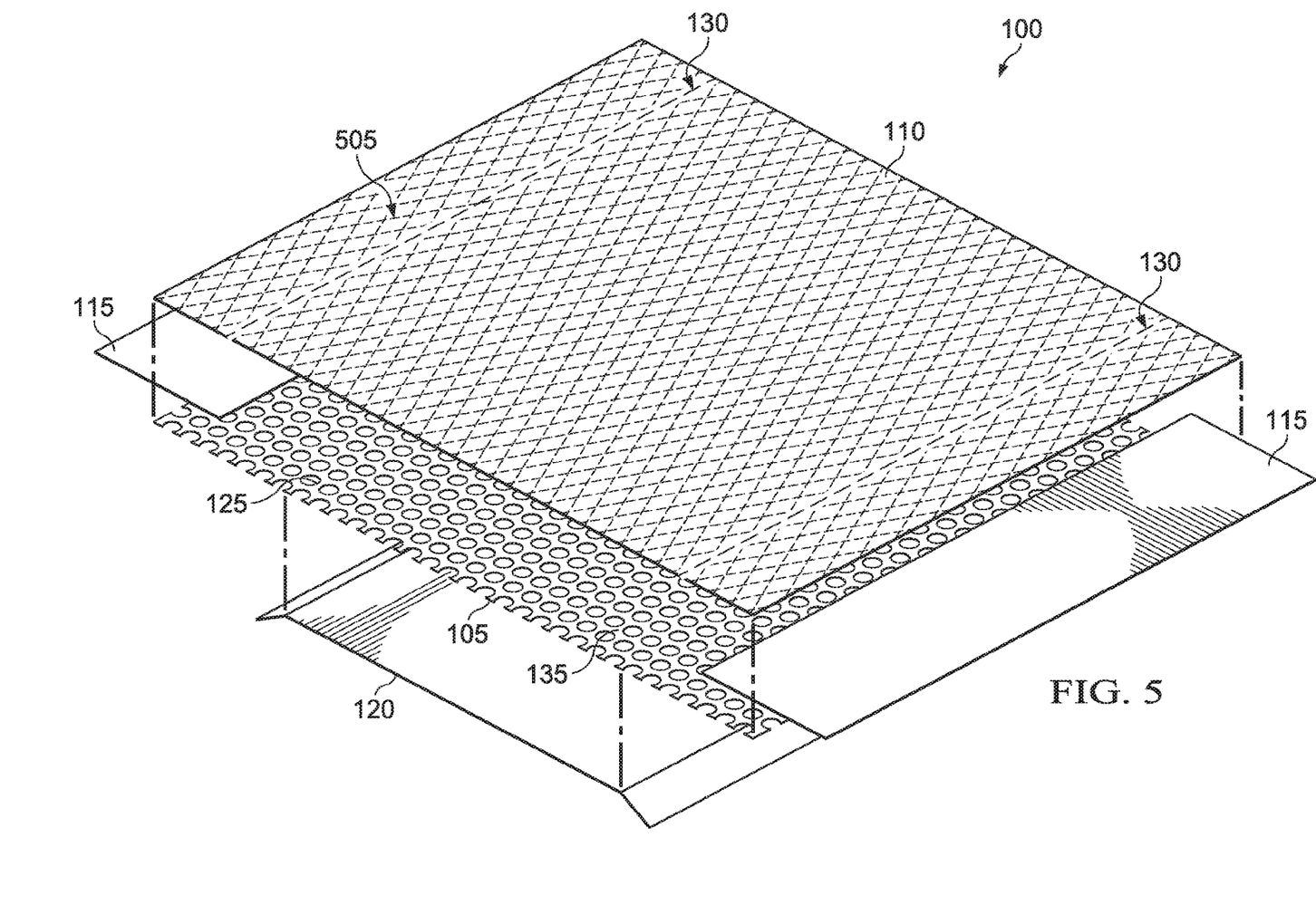
FIG. 5 is an assembly view of another example of a cover that can be applied to a tissue site.

FIG. 5 is an assembly view of another example of the cover 100, illustrating additional details that may be associated with some embodiments. For example, the shell layer 110 may comprise a plurality of apertures 505.

Figure 6:
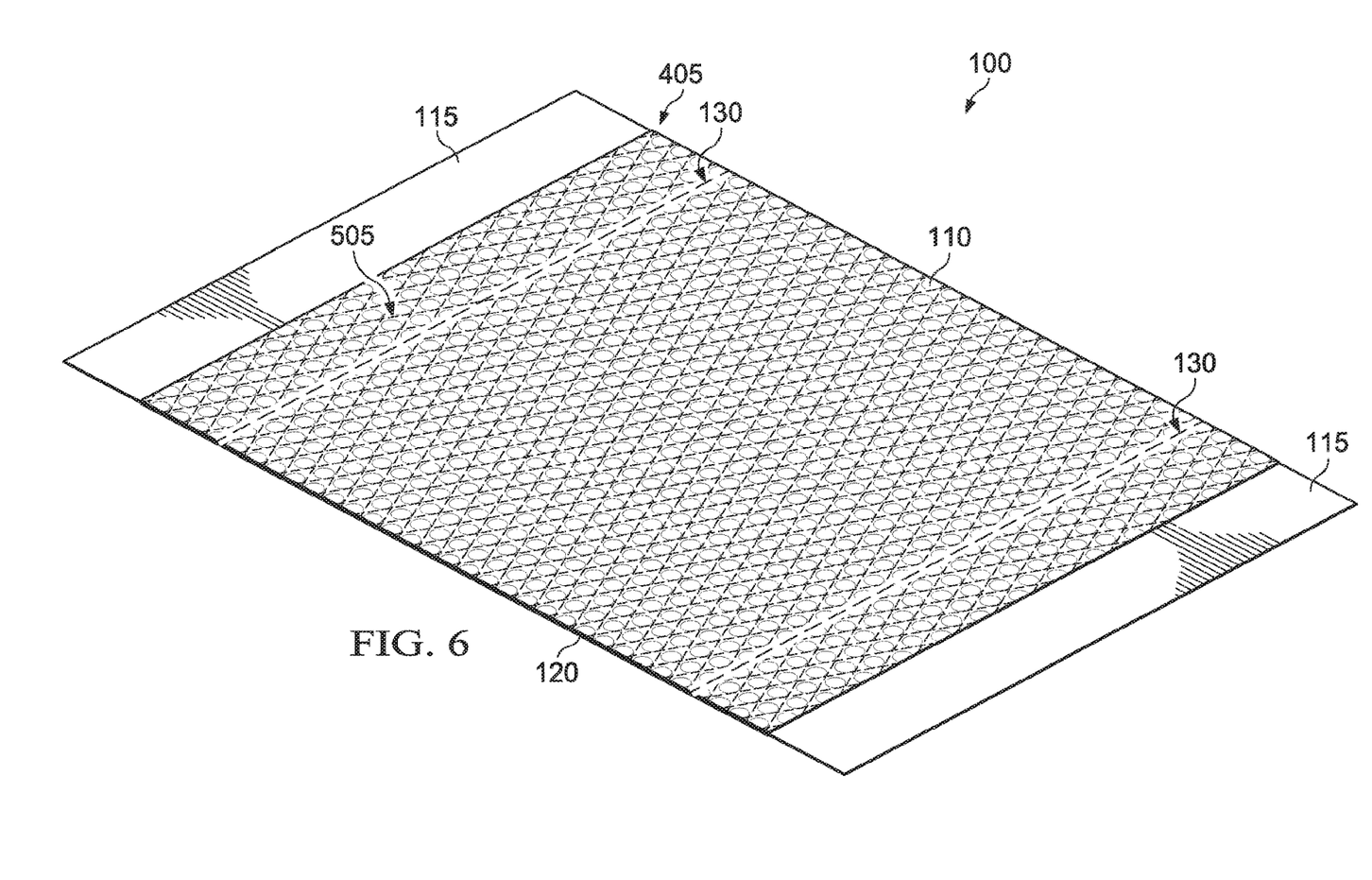
FIG. 6 is a perspective view of the assembled cover of FIG. 5.

FIG. 6 is an assembled view of the cover 100 of FIG. 5. As illustrated in the example of FIG. 6, the apertures 505 may be offset from the apertures 125.

Figure 7:
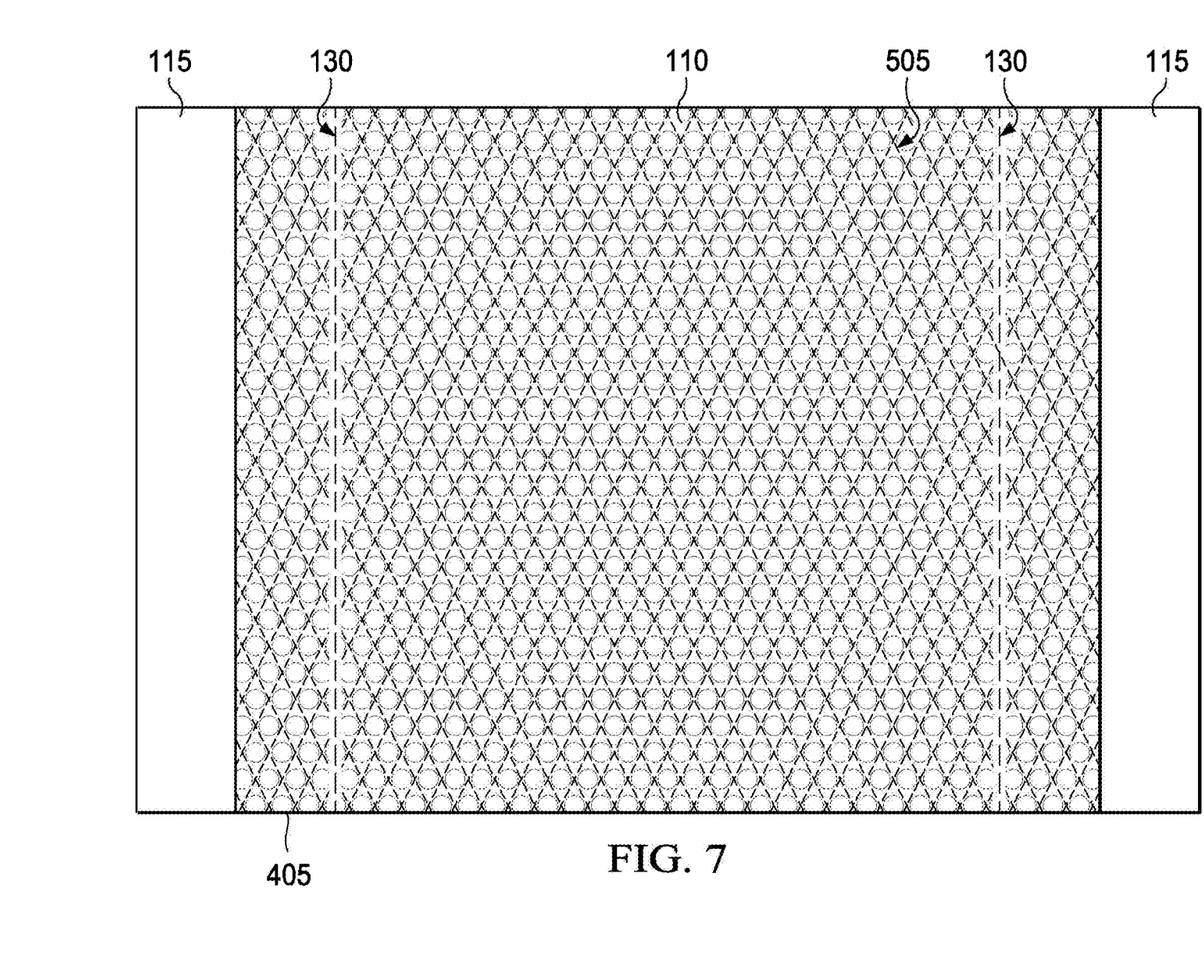
FIG. 7 is a top view of the cover of FIG. 6.

FIG. 7 is a top view of the cover 100 of FIG. 6, illustrating additional details that may be associated with some examples. As illustrated in the example of FIG. 7, the apertures 505 may be aligned with one or more bridges 135 between the apertures 125 in the contact layer 105.

In some embodiments, the apertures 505 may be characterized as slots or long holes having end bridges between the holes. A cut length of about 2 millimeters to about 5 millimeters may be suitable for some examples. The apertures 505 can be arranged to maintain the structural integrity of the shell layer 110. For example, the apertures 505 of FIG. 7 are arranged in linear patterns, which can intersect to form a diamond pattern in the shell layer 110. A tie length of about 2 millimeters to about 5 millimeters may be suitable for some examples.

A method of manufacturing some embodiments of the cover 100 may include perforating the contact layer 105 to form the apertures 125 in the contact layer 105. The apertures 125 may be formed by cutting or by application of local RF or ultrasonic energy, for example, or by other suitable techniques for forming a hole in the contact layer 105. The apertures 125 may be arranged in rows in some embodiments. For example, the contact layer 105 may have a first edge and a second edge parallel to the first edge, and the apertures 125 may be arranged so that at least one row has a midline parallel to the first edge. A second row may have also have a midline parallel to the second edge.

At least one handling bar may be disposed at least partially on the contact layer 105, and the shell layer 110 may be disposed on the contact layer 105, at least partially overlapping the handling bar.

The shell layer 110 may have an adhesive, which can be configured so that at least some of the adhesive is disposed adjacent to at least some of the apertures 125 in the contact layer 105. The adhesive may bond the shell layer 110 to the contact layer 105, securing the handling bar to the shell layer 110 and the contact layer 105.

The shell layer 110 and the contact layer 105 may be perforated in a linear pattern along an interior edge of the handling bar to form a sacrificial segment. The linear perforations preferably align with a midline (within an acceptable tolerance) of an outermost row of the apertures 125 in the contact layer 105, which can improve the separation of the sacrificial segment and reduce ragged edges. A tolerance between the linear perforations and the edge of the contact layer 105 may additionally or alternatively favor an alignment between the midline and the edge, which can minimize alignment with a tangent of the row of apertures 125 in the contact layer 105.

Additionally, or alternatively, the shell layer 110 may be perforated to form the apertures 505, which can overlay the bridges in the contact layer 105, as illustrated in the example of FIG. 7.

A release liner may then be disposed on the contact layer 105 in some examples. Alternatively, the release liner may be disposed on the contact layer 105 before perforating shell layer 110. For example, a suitable pressure may be applied to a roller die to cut through the shell layer 110 and the contact layer 105 without perforating the release liner. In some embodiments, a pressure in a range of about 750 pounds per square inch to about 1000 pounds per square inch may be suitable.

In use, the release liner 120 may be removed to expose the contact layer 105, which may be placed within, over, on, or otherwise proximate to a tissue site. For example, the contact layer 105 may be centered over a tissue site and a peripheral portion of the contact layer may be applied to an attachment surface adjacent to or proximate to the tissue site. The contact layer 105 may be sufficiently tacky to hold the cover 100 in position, while also allowing the cover 100 to be removed or re-positioned without significant trauma to the tissue site.

The handling bars 115 can facilitate handling the cover 100 until placed, and then the handling bars 115 may be removed. For example, the handling bars 115 of FIG. 4 may be removed by separating the sacrificial segments 405, which may be separated by tearing the contact layer 105 and the shell layer 110 along the apertures 215 and the apertures 130, respectively.

Removing the release liner 120 can also expose adhesive on the shell layer 110 through at least some of the apertures 125. Once the cover 100 is in a desired position, the adhesive may be pressed through the apertures 125 to bond the shell layer 110 to an attachment surface. The apertures 125 at the edges 205 may permit the adhesive to flow around the edges 205, which can enhance the adhesion to an attachment surface.

In some embodiments, the apertures 125 may be sized to control the amount of adhesive exposed through the contact layer 105. In some embodiments, the bond strength of the adhesive may vary in different locations of the cover 100. For example, the adhesive may have a lower bond strength in locations adjacent to apertures that are relatively larger, and may have a higher bond strength where apertures are smaller. Adhesive with lower bond strength in combination with larger apertures may provide a bond comparable to adhesive with higher bond strength in locations having smaller apertures.

In some applications, the contact layer 105, the shell layer 110, or both may have some elasticity, and the cover 100 may be intentionally or unintentionally stretched, either before or after placement on a tissue site. Tension in either the contact layer 105 or the shell layer 110 may cause shear on the adhesive, as well as tension on the tissue site. Some embodiments of the cover 100 may provide a means for reducing the shear and the tension. For example, some embodiments of the shell layer 110 may have a higher elastic modulus than the bond strength of the adhesive, and the apertures 505 may provide a means for decreasing the tensile modulus of the shell layer 110 so that the bond strength is greater than the tensile modulus. More particularly, the apertures 505 may move and open if the shell layer 110 is stretched or elongated, which can reduce the shear on the adhesive and any strain on the tissue site. The apertures 505 can also be disposed between the apertures 125 to prevent leak paths through the contact layer 105 and the shell layer 110. In other embodiments, the shell layer 110 may have a lower elastic modulus than the contact layer 105, and the contact layer 105 may comprise apertures disposed in the bridges 135 that are similar or analogous to the apertures 505.

Additionally or alternatively, the shell layer 110 may have a yield strength that is less than the bond strength of the adhesive. Consequently, the shell layer 110 can be stretched beyond its yield strength to plastically deform, and can be released without causing adhesive failure or traumatic tension on a tissue site. For example, the shell layer 110 can be configured to thin if it is stretched beyond its yield strength. In some embodiments, the shell layer 110 may comprise or consist essentially of polypropylene, polyesters, polyamides, or higher-density polyethylene. Polyurethane having a relatively low elasticity may also be suitable for some examples. The shell layer 110 may also be micro-perforated to increase breathability in some configurations.

In other examples, the shell layer 110 may additionally or alternatively be treated to create patterns of variable elasticity. For example, the shell layer 110 may comprise or consist of a polyurethane film treated with heat to form patterns of thick and thin areas. The thick sections may have a yield strength greater than the bond strength of the adhesive, and the thin section may have a yield strength that is less than the bond strength of the adhesive. For example, a film having a nominal thickness of about 150 microns may be treated to create a pattern of areas having about 50% of the nominal thickness.

In some embodiments, the shell layer 110 may comprise or consist essentially of a film that has been pre-stretched during an extrusion process, removing most of the elasticity from the film before cooling. The film may additionally or alternatively be formed from hydrophobic polymers to reduce changes from plasticization by moisture.

Strain indicators may be printed or otherwise disposed on some embodiments of the shell layer 110 to indicate acceptable levels of stretch, to indicate plastic deformation, or both. In some examples, a printed ink that fragments as it is deformed may be disposed on the shell layer 110. The printed ink may look thinner if the shell layer 110 is stretched, which can indicate the level of force being applied or caused by movement, such as movement of a joint.

The cover 100 can provide a sealed therapeutic environment proximate to a tissue site, substantially isolated from the external environment. The contact layer 105 may provide an effective and reliable seal against challenging anatomical surfaces, such as an elbow or heel, at and around a tissue site. Further, in some embodiments, the cover 100 may re-applied or re-positioned to eliminate creases and other discontinuities in the cover 100 or a tissue site, for example.

Figure 8:
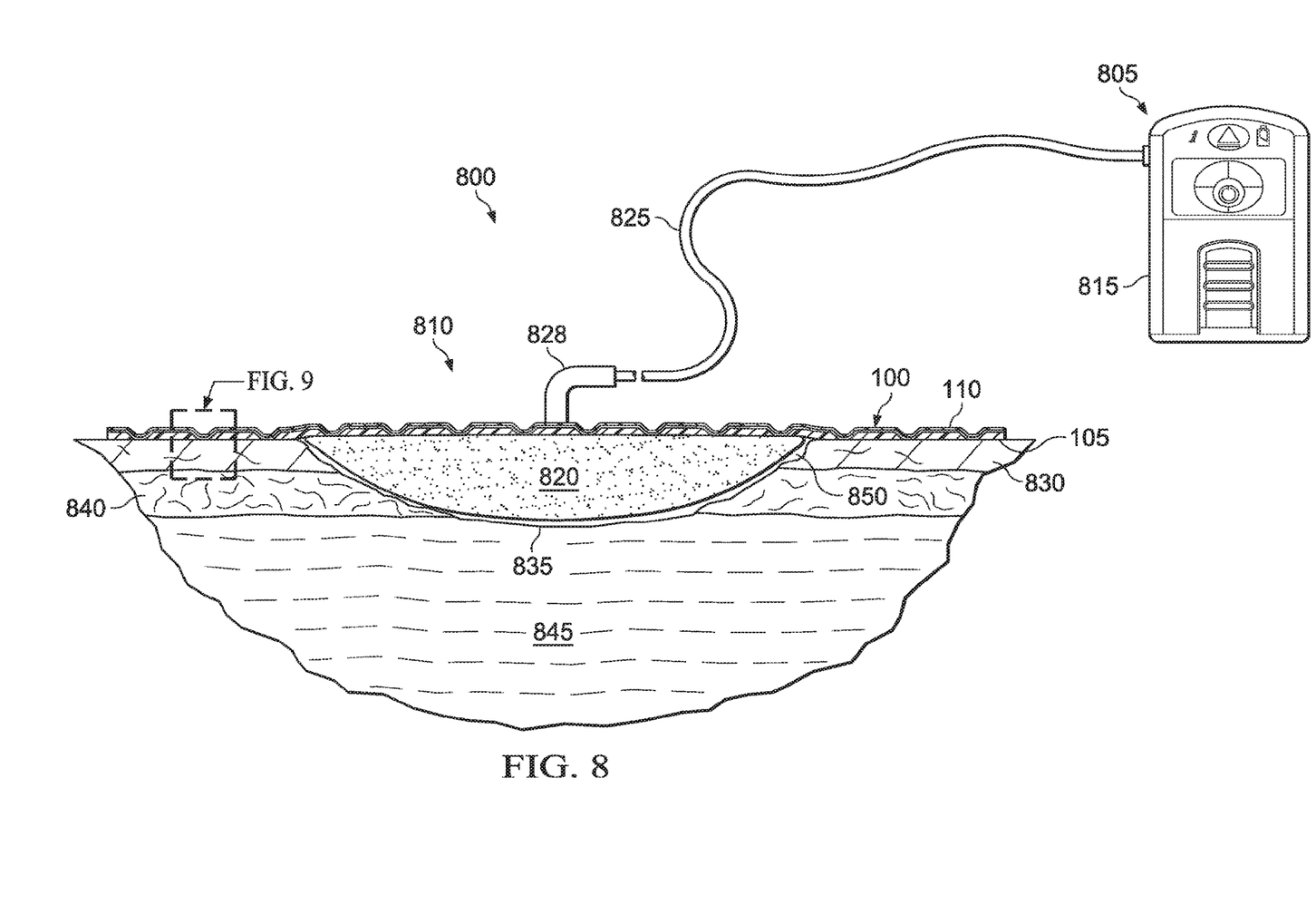
FIG. 8 is a schematic diagram illustrating an example of the cover of FIG. 1 used with a therapy system that can provide negative-pressure treatment to a tissue site.

FIG. 8 is a schematic diagram illustrating an example of the cover 100 used with a therapy system 800 that can reduce pressure in proximity to a tissue site. Clinical studies and practice have shown that reducing pressure in proximity to a tissue site can augment and accelerate growth of new tissue at the tissue site. The applications of this phenomenon are numerous, but it has proven particularly advantageous for treating wounds. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

The therapy system 800 may include a source or supply of negative pressure, such as a negative-pressure source 805, and one or more distribution components, such as a dressing or a fluid container. A distribution component is preferably detachable and may be disposable, reusable, or recyclable. A dressing, such as a dressing 810, and a fluid container, such as a container 815, are examples of distribution components that may be associated with some examples of the therapy system 800. As illustrated in the example of FIG. 8, the dressing 810 may comprise or consist essentially of the cover 100 and a tissue interface 820.

A fluid conductor 825 is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface 828 may facilitate coupling the fluid conductor 825 to the dressing 810. For example, such a dressing interface may be a SENSAT.R.A.C.™ Pad available from Kinetic Concepts, Inc. of San Antonio, Texas.

The therapy system 800 may also include a regulator or controller, and sensors to measure operating parameters and provide feedback signals to the controller indicative of the operating parameters. Some components of the therapy system 800 may be housed within or used in conjunction with other components, such as sensors, processing units, alarm indicators, memory, databases, software, display devices, or user interfaces that further facilitate therapy. For example, in some embodiments, the negative-pressure source 805 may be combined with a controller and other components into a therapy unit.

In general, components of the therapy system 800 may be coupled directly or indirectly. For example, the negative-pressure source 805 may be directly coupled to the container 815 and may be indirectly coupled to the dressing 810 through the container 815. Coupling may include fluid, mechanical, thermal, electrical, or chemical coupling (such as a chemical bond), or some combination of coupling in some contexts. For example, the negative-pressure source 805 may be electrically coupled to a controller and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 805, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 805 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 815 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The tissue interface 820 can be generally adapted to partially or fully contact a tissue site. The tissue interface 820 may take many forms, and may have many sizes, shapes, or thicknesses, depending on a variety of factors, such as the type of treatment being implemented or the nature and size of a tissue site. For example, the size and shape of the tissue interface 820 may be adapted to the contours of deep and irregular shaped tissue sites. Any or all of the surfaces of the tissue interface 820 may have an uneven, coarse, or jagged profile.

In some embodiments, the tissue interface 820 may comprise or consist essentially of a manifold. A manifold in this context may comprise or consist essentially of a means for collecting or distributing fluid across the tissue interface 820 under pressure. For example, a manifold may be adapted to receive negative pressure from a source and distribute negative pressure through multiple apertures across the tissue interface 820, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 820 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 820 may also vary according to needs of a prescribed therapy. For example, the tensile strength of foam may be increased for instillation of topical treatment solutions. The 25% compression load deflection of the tissue interface 820 may be at least 0.35 pounds per square inch, and the 65% compression load deflection may be at least 0.43 pounds per square inch. In some embodiments, the tensile strength of the tissue interface 820 may be at least 10 pounds per square inch. The tissue interface 820 may have a tear strength of at least 2.5 pounds per inch. In some embodiments, the tissue interface 820 may be foam comprised of polyols such as polyester or polyether, isocyanate such as toluene diisocyanate, and polymerization modifiers such as amines and tin compounds. In some examples, the tissue interface 820 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 820 may also vary according to needs of a prescribed therapy. For example, the thickness of the tissue interface 820 may be decreased to reduce tension on peripheral tissue. The thickness of the tissue interface 820 can also affect the conformability of the tissue interface 820. In some embodiments, a thickness in a range of about 5 millimeters to 10 millimeters may be suitable.

The tissue interface 820 may be either hydrophobic or hydrophilic. In an example in which the tissue interface 820 may be hydrophilic, the tissue interface 820 may also wick fluid away from a tissue site, while continuing to distribute negative pressure to the tissue site. The wicking properties of the tissue interface 820 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 820 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 820 may further serve as a scaffold for new cell-growth, or a scaffold material may be used in conjunction with the tissue interface 820 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Figure 9:
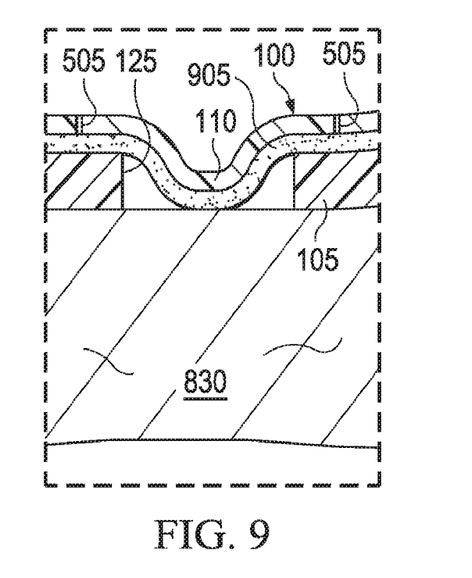
FIG. 9 is a detail view of the cover of FIG. 8.

In operation, the tissue interface 820 may be placed within, over, on, or otherwise proximate to a tissue site. If the tissue site is a wound, for example, the tissue interface 820 may partially or completely fill the wound, or it may be placed over the wound. The cover 100 may be placed over the tissue interface 820 and sealed to an attachment surface near a tissue site. For example, in FIG. 8 the cover 100 may be placed over the tissue interface 820 and epidermis 830 peripheral to a tissue site 835, which extends through the dermis 840 and into subcutaneous tissue 845. The contact layer 105 can retain the cover 100 in position, and as illustrated in the detail view of FIG. 9, pressure can be applied to the shell layer 110 to press an adhesive 905 on the shell layer 110 through the apertures 125 in the contact layer 105 into contact with the epidermis 830. In some embodiments, another adhesive may be disposed between the shell layer 110 and the adhesive 905. For example, an adhesive having a lower shear resistance than the adhesive 905 can decouple any elasticity in the shell layer 110 from the adhesive 905. Thus, the cover 100 can provide a sealed therapeutic environment 850 proximate to the tissue site 835, substantially isolated from the external environment, and the negative-pressure source 805 can reduce pressure in the sealed therapeutic environment 850.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

Negative pressure applied across the tissue site through the tissue interface 820 in the sealed therapeutic environment can induce macro-strain and micro-strain in the tissue site. Negative pressure can also remove exudate and other fluid from a tissue site, which can be collected in container 815.

The systems, apparatuses, and methods described herein may provide significant advantages. For example, the cover 100 can provide a high seal around and over a tissue site, while substantially reducing or eliminating trauma on removal. Additionally or alternatively, the cover 100 may facilitate handling and application to a tissue site. In some examples, the cover 100 may be stretched before or during application while maintaining a seal without significantly increasing tension on surrounding tissue or decreasing flexibility. These characteristics may be particularly advantageous for treating wounds with negative-pressure therapy.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the cover 100 may be separated from other components for manufacture or sale.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for covering a tissue site, the apparatus comprising:
   a contact layer having a first pattern of apertures and bridges;
   a shell layer having a first side and an opposite second side facing the contact layer, the shell layer having a second pattern of apertures overlaying the bridges; and
   adhesive disposed on the second side of the shell layer and exposed through the first pattern of apertures in the contact layer.

2. The apparatus of claim 1, wherein the adhesive has a bond strength greater than a tensile modulus of the shell layer.

3. The apparatus of claim 1, wherein the contact layer has an open area defined by the first pattern of apertures, and wherein the open area is in a range of about 40 percent to about 50 percent of the total area of the contact layer.

4. The apparatus of claim 1, wherein the second pattern of apertures comprises long holes, optionally wherein the second pattern of apertures comprises long holes having a length in a range of about 2 millimeters to about 5 millimeters, and optionally wherein the second pattern of apertures comprises end bridges between the long holes, the end bridges having a length in a range of about 2 millimeters to about 5 millimeters.

5. The apparatus of claim 1, wherein the first pattern of apertures comprises staggered rows.

6. The apparatus of claim 1, wherein the first pattern of apertures comprises staggered rows of circular holes, and wherein the second pattern of apertures comprises a diamond pattern of long holes.

7. The apparatus of claim 1, wherein:
the contact layer has a first modulus of elasticity;
the shell layer has a second modulus of elasticity; and
the first modulus of elasticity is less than the second modulus of elasticity.

8. The apparatus of claim 1, wherein the second pattern of apertures is configured to maintain structural integrity of the shell layer, and wherein the shell layer is configured to maintain a fluid seal around a tissue site.

9. The apparatus of claim 1, wherein the contact layer is a silicone gel, the shell layer is a polymer film, and the adhesive is an acrylic adhesive, and wherein the shell layer is permeable to water vapor but impermeable to liquid.

10. A dressing for treating a tissue site with negative pressure, the dressing comprising:
a manifold; and
the apparatus of claim 1 configured to cover the tissue site and the manifold.

11. A system for treating a tissue site with negative pressure, the system comprising:
the apparatus of claim 1; and
a negative-pressure source fluidly coupled to the dressing.

12. The apparatus of claim 1, wherein the second pattern of apertures in the shell layer are offset from the first pattern of apertures in the contact layer.

13. The apparatus of claim 1, wherein the second pattern of apertures in the shell layer are aligned with the bridges in the contact layer, and wherein the second pattern of apertures is disposed between the first pattern of apertures such that leak paths through the shell layer and the contact layer are prevented.

14. The apparatus of claim 1, wherein the shell layer has a yield strength less than the bond strength of the adhesive such that the shell layer can be stretched beyond its yield strength to plastically deform without causing adhesive failure.

15. An apparatus for covering a tissue site, the apparatus comprising:
a contact layer having a first pattern of holes;
a shell layer coupled to the contact layer; and
adhesive coated on a side of the shell layer facing the contact layer, the adhesive exposed through the first pattern of holes in the contact layer, the adhesive having a bond strength that is greater than the yield strength of the shell layer.

16. The apparatus of claim 15, wherein the shell layer has a yield strength less than the bond strength of the adhesive such that the shell layer can be stretched beyond its yield strength to plastically deform without causing adhesive failure.

17. The apparatus of claim 15, wherein:
the adhesive is acrylic adhesive; and
the shell layer is a film comprising or consisting essentially of polypropylene, polyesters, polyamides, or high-density polyethylene.

18. The apparatus of claim 15, wherein the shell layer is configured to thin if stretched.

19. The apparatus of claim 15, wherein the holes of the contact layer are configured to open under tension.

20. The apparatus of claim 15, wherein the shell layer comprises micro-perforations.

* * * * *